United States Patent [19]
Rossetti et al.

[11] 4,116,957
[45] Sep. 26, 1978

[54] RIFAMYCIN COMPOUNDS

[75] Inventors: Vittorio Rossetti; Leonardo Marsili; Carmine Pasqualucci, all of Milan, Italy

[73] Assignee: Archifar Industrie Chimiche del Trentino S.p.A., Rovereto, Italy

[21] Appl. No.: 831,224

[22] Filed: Sep. 7, 1977

[30] Foreign Application Priority Data

Oct. 18, 1976 [IT] Italy ................................ 2962 A/76

[51] Int. Cl.$^2$ ............................................ C07D 51/18
[52] U.S. Cl. ............................ 260/239.3 P; 424/270; 424/251
[58] Field of Search .................................. 260/239.3 P

[56] References Cited
FOREIGN PATENT DOCUMENTS 2,548,128  5/1976  Fed. Rep. of Germany .... 260/239.3 P
2,620,782  11/1976 Fed. Rep. of Germany .... 260/239.3 P

OTHER PUBLICATIONS

Casey et al., "J. Am. Chem. Soc." vol. 97, No. 21, pp. 6231–6236, (1975).
Dampier et al., "J. Am. Chem. Soc." vol. 97, No. 21, pp. 6254–6256, 7064–7069, (1975). Dampier et al., "J. Am. Chem. Soc." vol. 97, No. 21, pp. 7064–7069, (1975).

Primary Examiner—Natalie Trousof
Assistant Examiner—Robert T. Bond
Attorney, Agent, or Firm—Oblon, Fisher, Spivak, McClelland & Maier

[57] ABSTRACT

Rifamycin compounds having high antibacterial activity, comprising red-orange powders.

Such compounds are provided by reacting 3-bromo-rifamycin S with a compound having the formula $H_2N-CS-NH-X$.

2 Claims, No Drawings

RIFAMYCIN COMPOUNDS

This invention relates to novel rifamycin compounds having high antibiotic activity.

In German Patent Application DOS No. 2,548,128, in J. Am. Chem. Soc. 97 (21), 6231; in J. Am. Chem. Soc. 97 (21), 6254, and in J. Am. Chem. Soc. 98 (22), 7064, there are disclosed a compound having the formula

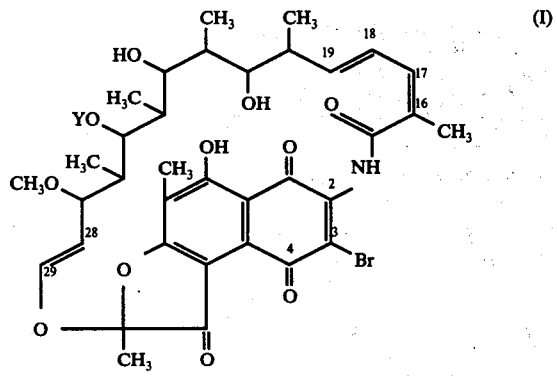

and its 16, 17, 18, 19 tetrahydroderivatives and 16, 17, 18, 19, 28, 29 hexahydroderivatives, wherein Y is —H or —COCH$_3$.

This invention relates to rifamycin compounds having the formula

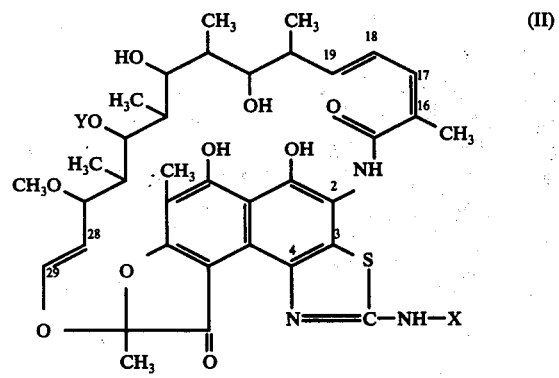

and its 16, 17, 18, 19 tetrahydroderivatives and 16, 17, 18, 19, 28, 29 hexahydroderivatives, wherein Y is —H or —COCH$_3$ and X is selected from the group comprising hydrogen; alkyl having 1–12 C atoms; alkoxyalkyl having 3–4 C atoms; hydroxyalkyl having 2–4 C atoms; N,N-dialkylamino alkyl having 4–6 C atoms; arylalkyl hydrocarbon having 7–8 C atoms; cycloalkyl having 3–7 C atoms; alkenyl having 3–6 C atoms; phenyl; arylalkyl hydrocarbon having 7 C atoms substituted in the aromatic ring with a radical selected from the group comprising halogen, methyl, ethyl, propyl, butyl, methoxyl, N,N-dimethylammino; phenylmethylimino; 5-member heterocycle having a heteroatom selected from the group comprising O and S; 5-member heterocycle having three N-heteroatoms; 6-member heterocycle with two N-heteroatoms; furfuryl-2-methylimino.

The compounds of formula (II) comprise red-orange powders, unsoluble in water and soluble in most of the organic solvents.

Such compounds are obtained by reacting a compound of formula I with a compound having the formula

wherein X is as defined for the compound of formula (II), the reaction being performed by dissolving the compound of formula (I) in a solvent selected from the group comprising methanol, ethanol, tetrahydrofuran, and reacting it with the compound of formula (III) at a temperature in the range of −5° C—+40° C and for a time of between 5 minutes and 25 hours.

In order that the present invention be more clearly understood, some exemplary embodiments thereof will now be illustrated by mere way of unrestrictive example.

Chromatographies on thin layer were performed on silica gel plates, using a benzene-methanol-ethyl acetate mixture (20:8:7) as eluent.

EXAMPLE 1

10 g 3-bromo-rifamycin S were dissolved in 50 ml methanol and under stirring at 7° C were added with 3 g N-methyl-thiourea. After 10 minutes, a red crystalline solid was separated, filtered and washed with methanol. The product was dissolved in 100 ml chloroform, filtered and evaporated to dryness at reduced pressure, crystallized from 40 ml methanol and vacuum dried at 40° C. 6.2 g red crystals were obtained, comprising the compound of formula II, wherein X is methyl.

I.R. 3375, 3175, 1723, 1625, 1565, 1515, 1315(b), 1240, 1160, 1125, 1105(Sh), 1065, 1020, 980, 955, 920, 885 and 810 cm$^{-1}$.

Rf = 0.58

| Elementary analysis for C$_{39}$H$_{49}$N$_3$O$_{11}$S: | | | | | |
|---|---|---|---|---|---|
|  | C | H | N | O | S |
| Calculated, % | 60.99 | 6.44 | 5.47 | 22.92 | 4.18 |
| Found, % | 60.93 | 6.28 | 4.83 | 22.63 | 4.07 |

$\lambda_{max}$ 430 nm ($E_{1cm}^{1\%}$ = 150.6)

The $^{13}$C NMR spectrum in CDCl$_3$ shows a signal at $\delta$ = 183.5 p.p.m. (using tetramethylsilane as internal standard) attributable to the heterocyclic C— atom.

The same product (6.6 g) was obtained by using tetrahydrofuran as a solvent at room temperature for 25 minutes.

EXAMPLE 2

10 g 3-bromo-rifamycin S were dissolved in 50 ml methanol, the solution was cooled to 7° C and 3 g N-phenyl-thiourea were added. The solution was stirred for 3 hours at room temperature, then added with 0.5 g manganese dioxide. Stirring was continued overnight, then adding 1 g N-phenyl-thiourea. After 1 hour the solution was filtered and the filtrate dropwise poured into 20 ml water. The separated solid was filtered and washed with water, and suspended with chloroform. The organic solution was repeatedly washed with water, dried and evaporated to dryness under reduced pressure.

9.5 g residue were obtained, of which 5 g were purified by chromatography on column filled up with 230 g silica gel and eluting with benzene-acetone mixture (8:2). Thus, 0.4 g product were obtained, comprising a chromatographycally pure compound of formula II as yellow-orange crystals, where X is phenyl.

I.R. 3350, 3150, 1720, 1640, 1630, 1615, 1580, 1510, 1315(b), 1260(Sh), 1240, 1160, 1125, 1105(Sh), 1065, 1025, 975, 950, 920, 885, 805, 755 and 700 cm$^{-1}$.

Rf = 0.51

$\lambda_{max}$ 433 nm ($E_{1cm}^{1\%}$ = 116.4).

EXAMPLE 3

10 g 3-bromo-rifamycin S were dissolved in 50 ml methanol, the solution was cooled to 3° C and added with 4 g N-cyclohexylthiourea. The reaction mixture was kept at 5° C and stirred for 50 minutes. The mixture was diluted with 200 ml chloroform, added with 100 ml water and decanted, the organic layer was anhydrified on sodium sulphate and evaporated to small volume, then diluting with 100 ml toluene at 80° C. The mixture was allowed to crystallize by cooling, then filtered and yielding 6.7 g quite pure product. 3 g of this product were purified by chromatography on silica gel column, eluting with benzene-acetone mixture (75:25), thus obtaining 1.7 pure product comprising the compound of formula II as yellow-orange crystals, wherein X is cyclohexyl.

I.R. 3375, 3175, 1720, 1615, 1570, 1515, 1315, 1260(Sh), 1240, 1165, 1025, 980, 950, 920, 890, 810, 795 and 770 cm$^{-1}$.

Rf = 0.61

$\lambda_{max}$ 431 nm ($E_{1cm}^{1\%}$ = 152.6).

EXAMPLE 4

A solution of 10 g 3-bromo-rifamycin S in 50 ml methanol was reacted at 0° C with 2.5 g N-allyl-thiourea. After stirring for 4 hours at 3° C, the solution was diluted with 100 cc chloroform; the mixture was washed with water, the organic layer was decanted and vacuum dry evaporated. The residue was suspended with 100 ml ethyl acetate, filtered and evaporated again and then crumbled with isopropyl ether. 7.3 g raw product were obtained, of which 5 g were purified by chromatography on silica gel column (benzene-acetone eluent 8:2), obtaining 2.7 g pure product, comprising the compound of formula II as red-brick crystals, wherein X is allyl.

I.R. 3350, 3175, 1730, 1645(Sh), 1615, 1568, 1530, 1515, 1315, 1240, 1160, 1125, 1090, 1065, 1055(Sh), 1023, 980, 950, 920, 885, 810 and 765 cm$^{-1}$.

Rf = 0.62

| Elementary analysis for $C_{41}H_{51}N_3O_{11}S$: | | |
|---|---|---|
| C | H | S |
| Calculated, % 62.03 | 6.46 | 4.04 |
| Found, % 62.02 | 6.33 | 4.12 |

$\lambda_{max}$ 430 nm ($E_{1cm}^{1\%}$ = 164.2).

EXAMPLE 5

10 g 3-bromo-rifamycin S were dissolved in 50 ml methanol and after cooling to 4° C, 4 g N-(p-chlorobenzyl)-thiourea were added under good stirring, the reaction mixture was kept under stirring for 1 hour at 5° C, further 2 g N-(p-chlorobenzyl)-thiourea were added and stirring was continued for another hour. The mixture was diluted with 200 ml chloroform, 200 ml water were added and after decanting the organic layer was repeatedly washed with water and evaporated to dryness. The residue, as suspended with isopropyl ether and filtered, yielded 12.9 g raw product, of which 3 g were purified by chromatography on silica gel column(-benzene-acetone solvent 75:25), obtaining 0.8 g pure product comprising the compound of formula II, wherein X is 4-chloro-benzyl.

I.R. 3375, 3200, 1725, 1615, 1570, 1515, 1320, 1245, 1160, 1099, 1070, 1023, 980, 955, 922, 890, 810 and 765(Sh) cm$^{-1}$.

Rf = 0.64

$\lambda_{max}$ 430 nm ($E_{1cm}^{1\%}$ = 141.4).

EXAMPLE 6

Under stirring at 5° C, a solution of 10 g 3-bromo-rifamycin S was added with 4 g N-(2-hydroxyethyl)-thiourea. The reaction mixture was stirred for 25 minutes at 4° C and isolated, then extracting with chloroform a raw product (9.4 g). 3 g raw product, as purified by chromatography on silica gel column, using as eluent a mixture of benzene-acetone-methanol (70:30:5), yielded 0.9 pure product comprising the compound of formula II, wherein X is 2-hydroxy-ethyl.

I.R. 3350(b), 3175, 1720, 1620, 1565, 1515, 1315, 1245, 1165, 1125, 1065, 1025, 980, 955, 925, 895 and 810 cm$^{-1}$.

Rf = 0.53

$\lambda_{max}$ 431 nm ($E_{1cm}^{1\%}$ = 160.3)

EXAMPLE 7

20 g 3-bromo-rifamycin S were dissolved in 100 ml methanol, the solution was cooled to 10° C and added with 4 g thiourea under stirring. The reaction mixture was kept at 10° C for 40 minutes and dropwise poured into 300 ml water, vigorously stirring. A solid was separated, filtered and washed with water. The mother liquors were whipped with 50 ml ethyl acetate, thus crystallizing a red solid that, after filtering, was combined with the solid separated from water, and the whole was crystallized from 150 ml boiling ethyl acetate. Thus, 11.5 g product of formula II as pure red crystals were obtained, wherein X is hydrogen.

I.R. 3325, 1725, 1715, 1660(Sh), 1645, 1632(Sh), 1565, 1515, 1315, 1265, 1240, 1160, 1125, 1065, 1025, 980, 965, 920, 888 and 810 cm$^{-1}$.

Rf = 0.57

| Elementary analysis for $C_{38}H_{47}N_3O_{11}S$: | | |
|---|---|---|
| C | H | S |
| Calculated, % 60.54 | 6.28 | 4.25 |
| Found, % 60.39 | 6.24 | 4.12 |

$\lambda_{max}$ 426 nm ($E_{1cm}^{1\%}$ = 199.6)

The same product (8.1 g) was obtained by using ethanol as a solvent at room temperature for 20 minutes.

EXAMPLE 8

10 g 3-bromo-rifamycin S dissolved in 50 ml methanol were cooled to 4° C and added with 4 g N-(2-methyl-allyl)-thiourea. Repeating the same process as for Example 3, to 10 g raw product were obtained, of which 3 g were purified by chromatography on silica gel column, using a mixture of benzene-acetone 75:25 as eluent, thus obtaining 1 g pure product comprising the compound of formula II, wherein X is 2-methyl-allyl.

I.R. 3375, 3200, 1725, 1615, 1566, 1515, 1322, 1245, 1163, 1070, 1025, 980, 955, 920, 890 and 810 cm$^{-1}$.

Rf = 0.67

$\lambda_{max}$ 430 nm ($E_{1cm}^{1\%}$ = 157.2).

EXAMPLE 9

10 g 3-bromo-rifamycin S dissolved in 50 ml methanol were reacted for 15 minutes at 5° C with 4 g N-ter-butyl-thiourea. Repeating the process as for Example 3, 11.1 g raw product were obtained, of which 3 g were purified by chromatography on silica gel column, using a mixture of benzene-acetone (8:2) as eluent, thus obtaining 1.2 g pure product comprising the compound of formula II, wherein X is tert-butyl.

I.R. 3375, 3200, 1720, 1645(Sh), 1610, 1565, 1515, 1315, 1260(Sh), 1240, 1210(Sh), 1160, 1125, 1105, 1065, 1025, 978, 955, 920, 885, 810, 795 and 765 cm$^{-1}$.

Rf = 0.59

$\lambda_{max}$ 428 nm ($E_{1cm}^{1\%}$ = 170.3).

EXAMPLE 10

10 g 3-bromo-rifamycin S dissolved in 50 ml methanol were reacted for 10 minutes at 5° C with 4 g N-isobutyl-thiourea. The reaction mixture, as treated for the preceding examples, yielded 10.5 g raw residue, of which 3 g were purified by chromatography on silica gel column, using a mixture of benzene-acetone (75:25) as eluent, thus obtaining 1.7 g pure product of formula II, wherein X is 2-methyl-propyl.

| | Elementary analysis for $C_{42}H_{55}N_3O_{11}S$: | | | |
|---|---|---|---|---|
| | C | H | N | S |
| Calculated, % | 62.28 | 6.86 | 5.19 | 3.96 |
| Found, % | 62.20 | 7.04 | 4.87 | 3.82 |
| Rf = 0.61 | | | | |

EXAMPLE 11

10 g 3-bromo-rifamycin S dissolved in 50 ml methanol were reacted for 30 minutes at 3° C with 4 g N-ethyl-thiourea. Repeating the process as for Example 3, 9.9 g residue were obtained, of which 3 g were purified by chromatography on silica gel column, using a mixture of benzene-acetone (75:25) as eluent. Thus, 2.1 g pure product of formula II were obtained, wherein X is ethyl.

I.R. 3370, 3180, 1720, 1620, 1570, 1515, 1315, 1260(Sh), 1244, 1160, 1125, 1105, 1095, 1068, 1025, 980, 965, 920, 886, 809 and 765 cm$^{-1}$.

Rf = 0.58

$\lambda_{max}$ 431 nm ($E_{1cm}^{1\%}$ = 174.4).

EXAMPLE 12

In a solution of 10 g 3-bromo-rifamycin S in 50 ml methanol 4 g N-isopropyl-thiourea were added at 3° C and the reaction mixture was stirred for 30 minutes. Repeating the process as for the preceding examples, 10.1 g raw product were obtained, of which 3 g were purified by chromatography on silica gel column, using a mixture of benzene-acetone (75:25) as eluent, thus obtaining 1.6 g pure product of formula II, wherein X is isopropyl.

I.R. 3310, 3175, 1720(b), 1615, 1565, 1515, 1312, 1240, 1160, 1130, 1105, 1065, 1025, 978, 950, 920, 885 and 806 cm$^{-1}$.

| | Elementary analysis for $C_{41}H_{53}N_3O_{11}S$: | | | |
|---|---|---|---|---|
| | C | H | N | S |
| Calculated, % | 61.86 | 6.71 | 5.28 | 4.03 |
| Found, % | 62.25 | 6.95 | 4.83 | 3.85 |
| Rf = 0.59 | | | | |

| | Elementary analysis for $C_{41}H_{53}N_3O_{11}S$: | | | |
|---|---|---|---|---|
| | C | H | N | S |

$\lambda_{max}$ 430 nm ($E_{1cm}^{1\%}$ = 164.4).

EXAMPLE 13

A solution as obtained by dissolving 10 g 3-bromo-rifamycin S in 50 ml methanol was reacted for 25 minutes at 4° C with 4 g N-propyl-thiourea, and proceeding as for the preceding examples 9 g raw product were obtained, of which 3 g were purified by chromatography on silica gel column, using a mixture of benzene-acetone (8:2) as eluent, thus obtaining 1.9 g pure product of formula II, wherein X is n-propyl.

I.R. 3375(Sh), 3175, 1720, 1620, 1570, 1515, 1315, 1265, 1245, 1165, 1108(Sh), 1070, 980, 965, 925, 890 and 810 cm$^{-1}$.

Rf = 0.57

$\lambda_{max}$ 430 nm ($E_{1cm}^{1\%}$ = 162.8).

EXAMPLE 14

A solution of 10 g 3-bromo-rifamycin S in 50 ml methanol was reacted for 15 minutes at 5° C with 4 g N-sec-butyl-thiourea. The process was repeated as previously described, obtaining 10.3 g solid residue, of which 3 g were purified by chromatography on silica gel column, using a mixture of benzene-acetone (75:25) as eluent, and thus obtaining 1.8 g pure product of formula II, wherein X is 2-butyl.

I.R. 3325, 3175, 1720, 1615, 1565, 1515, 1315, 1260(Sh), 1240, 1160, 1125, 1105, 1065, 1025, 975, 955, 920, 886, 808 and 765 cm$^{-1}$.

Rf = 0.57

$\lambda_{max}$ 430 nm ($E_{1cm}^{1\%}$ = 159.2).

EXAMPLE 15

10 g 3-bromo-rifamycin S dissolved in 50 ml methanol were reacted with 5 g N-dodecyl-thiourea at 4° C for 4 hours, then for 1 hour at 25° C. The reaction mixture was treated as for the preceding example to obtain 10.9 g residue of rubbery product, of which 3 g were purified by percolation on silica gel column, using a mixture of acetone-benzene (2:8) as eluent, thus obtaining 0.8 g pure product of formula II, wherein X is dodecyl.

I.R. 3360(b), 3175, 1720, 1615, 1565, 1515, 1315, 1240, 1160, 1065, 1025, 980, 950, 920, 885 and 808 cm$^{-1}$.

Rf = 0.66

$\lambda_{max}$ 418 nm and 430 nm ($E_{1cm}^{1\%}$ = 131.2).

EXAMPLE 16

10 g 3-bromo-rifamycin S dissolved in 50 ml methanol were reacted for 2 hours at 3° C with 4 g furfural-thiosemicarbazone. Proceeding as described in the preceding examples, a raw product was obtained which, crystallized from benzene, yielded 3.6 g pure product of formula II, wherein X is

I.R. 3325, 3200(Sh), 1725, 1640(Sh), 1620, 1550, 1310, 1265, 1235, 1160, 1125, 1065, 1055, 1015, 980, 950, 890, 830, 810 and 765 cm$^{-1}$.

Rf = 0.27

$\lambda_{max}$ 317 nm ($E_{1cm}^{1\%}$ = 225.5) and 390 nm (213.2).

EXAMPLE 17

A solution of 5 g 3-bromo-rifamycin S in 50 ml methanol was reacted at 2° C with 2 g benzaldehyde thiosemicarbazone. The temperature was then risen to 22° C and the solution stirred for 12 hours. The reaction mixture was extracted with 200 ml chloroform, washed three times with 150 ml water and the organic layer was evaporated to dryness at reduced pressure. The residue was suspended with 100 ml boiling isopropanol and allowed to stand for 12 hours at 5° C. The suspension was filtered and after further 24 hours of standing at 5° C the filtrate separated a rubbery solid. The liquid was decanted and the solid suspended with 200 ml ethyl acetate. The ethyl acetate solution was washed five times with 50 ml buffer phosphate pH 7.4, dried on sodium sulphate and dry evaporated. A residue was obtained, which upon crumbling with isopropyl ether yielded 3 g product of formula II, wherein X is —N=•CH—$C_6H_5$.

I.R. 3375, 3200(Sh), 1725, 1645(Sh), 1620, 1585, 1550, 1310, 1265, 1235, 1165, 1068, 1055, 1020, 1010, 980, 950, 895, 810, 765 and 700 cm$^{-1}$.

Rf = 0.30.

$\lambda_{max}$ 387 nm ($E_{1cm}^{1\%}$ = 248).

EXAMPLE 18

As described in Example 15, 10 g 3-bromo-rifamycin S were reacted with N-butyl-thiourea, and proceeding as disclosed therein, 1.6 g pure product of formula II were isolated, wherein X is n-butyl.

I.R. 3375, 3200, 1720, 1620, 1570, 1515, 1315, 1245, 1160, 1125, 1105, 1068, 1025, 980, 950, 915, 890, 810 and 765 cm$^{-1}$.

Rf = 0.60

| Elementary analysis for $C_{42}H_{55}N_3O_{11}S$: | | | |
|---|---|---|---|
| C | H | N | S |
| Calculated, % 62.28 | 6.84 | 5.19 | 3.96 |
| Found, % 62.54 | 6.91 | 4.86 | 3.71 |

$\lambda_{max}$ 430 nm ($E_{1cm}^{1\%}$ = 161.5), 308 nm ($E_{1cm}^{1\%}$ = 312.5).

EXAMPLE 19

10 g 3-bromo-rifamycin S were reacted in 50 ml methanol with 4 g N-benzyl-thiourea at room temperature for 1 hour. The procedure was then followed as described in the preceding examples to obtain 7 g raw product that, purified by chromatography on column as above described, yielded 4.5 g pure product of formula II, wherein X is benzyl.

I.R. 3350, 3175, 1720, 1615, 1570, 1515, 1315, 1260(Sh), 1240, 1160, 1125, 1065, 1025, 980, 950, 915, 885, 810, 780 and 705 cm$^{-1}$.

Rf = 0.66

| Elementary analysis for $C_{45}H_{53}N_3O_{11}S$: | | | |
|---|---|---|---|
| C | H | N | S |
| Calculated, % 64.04 | 6.33 | 4.98 | 3.80 |
| Found, % 64.53 | 6.59 | 4.74 | 3.63 |

$\lambda_{max}$ 430 nm ($E_{1cm}^{1\%}$ = 150.3), 308 nm ($E_{1cm}^{1\%}$ = 309.7).

EXAMPLE 20

A solution of 10 g 3-bromo-rifamycin S in 50 ml methano was added with 4 g N-phenetyl-thiourea at 4° C under stirring. After 40 minutes at 10° C the reaction mixture was treated as for Example 3, obtaining 10.6 g raw product that, chromatographied as above described, yielded 2.2 g pure product of formula II, wherein X is 2-phenyl-ethyl.

Rf = 0.60

| Elementary Analysis for $C_{46}H_{55}N_3O_{11}S$: | | | |
|---|---|---|---|
| C | H | N | S |
| Calculated, % 64.39 | 6.46 | 4.90 | 3.74 |
| Found, % 63.53 | 6.33 | 4.20 | 3.65 |

EXAMPLE 21

10 g 3-bromo-rifamycin S dissolved in 40 ml methanol were cooled to 0° C, then adding a solution of 4 g N-(2-tetrahydrofurylmethyl)-thiourea in 10 ml methanol. The solution was stirred for 3 hours at 10° C and following the procedure as previously described, 9.5 g raw product were obtained, of which 3 g were purified by chromatography on column as above described, obtaining 1 g product of formula II, wherein X is 2-tetrahydrofuryl methyl.

Rf = 0.50

$\lambda_{max}$ 430 nm ($E_{1cm}^{1\%}$ = 151), 305 nm ($E_{1cm}^{1\%}$ = 283)

I.R. 3400(b), 3200(b), 1730(Sh), 1715, 1650(Sh), 1620, 1570, 1520, 1315(b), 1260(Sh), 1240, 1160, 1100(Sh), 1065, 1020, 975, 950, 915, 885 and 805 cm$^{-1}$.

EXAMPLE 22

A solution of 10 g 3-bromo-rifamycin S in 50 ml methanol was added with 4 g N-(N,N-diethylaminoethyl)-thiourea at 10° C. After stirring for 6 hours at 23° C, the reaction mixture was treated as described in the preceding examples, obtaining 7.7 g raw product, purified by chromatography on column as above described, thus obtaining a residue that crystallized from benzene yielded 1.03 g product of formula II, wherein X is N,N-diethylaminoethyl.

Rf = 0.50

$\lambda_{max}$ 425 nm ($E_{1cm}^{1\%}$ = 180), 303 nm ($E_{1cm}^{1\%}$ = 316).

EXAMPLE 23

4 g N-(1,2,4-triazol-3-yl)-thiourea were reacted with 10 g 3-bromo-rifamycin S in 10 ml methanol at 20° C for 24 hours, then proceeding as above described and obtaining 7.9 g raw product that was purified by chromatography on column as for the preceding examples, thus obtaining 1.05 g product of formula II, wherein X is 1,2,4-triazol-3-yl.

Rf = 0.52

$\lambda_{max}$ 426 nm ($E_{1cm}^{1\%}$ = 185), 304 nm ($E_{1cm}^{1\%}$ = 308)

I.R. 3450(b), 1720, 1650, 1570, 1530, 1315, 1265, 1240, 1230(Sh), 1160, 1100, 1060, 1020, 980, 950, 915, 885 and 805 cm$^{-1}$.

EXAMPLE 24

10 g 3-bromo-rifamycin S were dissolved in 50 ml methanol, the solution was cooled to 0° C, and 5 g N-(1,3-dimethyl-2,6-dioxo-1,2,3,6-tetrahydropyrimidine-4-yl)-thiourea were charged, then allowing the temperature to rise to room temperature and stirring for 5 hours. The reaction mixture was treated as above described, obtaining 6.7 g product that purified by chromatography on column yielded 0.9 g product of formula II, wherein X is 1,3-dimethyl-2,6-dioxo-1,2,3,6-tetrahydropyrimidine-4-yl.

Rf = 0.72

EXAMPLE 25

4 g N-furfuryl-thiourea were reacted with 10 g 3-bromo-rifamycin S in 50 ml methanol at 3° C for 5 hours and, proceeding as above described, 10.3 g raw product were obtained, that crystallized twice from benzene yielded 3.9 g product of formula II, wherein X is furfuryl.

Rf = 0.58

EXAMPLE 26

10 g 3-bromo-rifamycin S were reacted in 50 ml methanol with 4 g N-cyclohexylmethyl-thiourea at 15° C for 70 minutes. The product was isolated as above described, obtaining 12.4 g raw product that, purified by chromatography, yielded 3.3 g product of formula II, wherein X is cyclohexylmethyl.

Rf = 0.62

$\lambda_{max}$ 427 nm ($E_{1cm}^{1\%}$ = 154), 307 nm ($E_{1cm}^{1\%}$ = 334)

I.R. 3375(b), 3175(b), 1735(Sh), 1720, 1650(Sh), 1620, 1568, 1520, 1315(b), 1285(Sh), 1260(Sh), 1240, 1158, 1065, 1020, 975, 945, 915, 885 and 805 cm$^{-1}$.

EXAMPLE 27

5 g 3-bromo-rifamycin S dissolved in 50 ml methanol were reacted at 4° C with 2 g N-cyclopropyl-thiourea for 70 minutes. The raw product was isolated as above described and crystallized from benzene to yield 1.8 g product of formula II, wherein X is cyclopropyl.

Rf = 0.57

$\lambda_{max}$ 428 nm ($E_{1cm}^{1\%}$ = 183), 307 nm ($E_{1cm}^{1\%}$ = 346)

I.R. 3325(b), 3150(b), 1730, 1715, 1650(Sh), 1610, 1575, 1565, 1520, 1315(b), 1255(Sh), 1238, 1155, 1100, 1065, 1025, 973, 945, 910, 870 and 805 cm$^{-1}$.

EXAMPLE 28

A solution of 50 g 3-bromo-rifamycin S in 250 ml methanol was added at 10° C with a solution of 20 g N-(2-dimethoxy-ethyl)-thiourea in 100 ml methanol. The solution was stirred at 13° C for 40 minutes, diluted with 500 ml dichloromethane, repeatedly washed with water, then dried on sodium sulphate, vacuum concentrated to about 150 ml, diluted with 300 ml benzene, and dichloromethane was vacuum removed. Thus, 32 g product of formula II were crystallized, wherein X is 2-dimethoxy-ethyl.

Rf = 0.61

$\lambda_{max}$ 430 nm ($E_{1cm}^{1\%}$ = 152), 307 nm ($E_{1cm}^{1\%}$ = 301)

I.R. 3450, 3300, 3200, 1745, 1635, 1605, 1550, 1515, 1315, 1245, 1223(Sh), 1160, 1125, 1080, 1045, 1020, 990, 975, 955, 940, 905, 885, 855 and 805 cm$^{-1}$.

EXAMPLE 29

5 g 3-bromo-rifamycin S in 50 ml methanol were reacted with 2 g N-(2-methoxy-benzyl)-thiourea at 0° C for 2 hours. As described in Example 3, a raw product was isolated, that purified by chromatography on column yielded 1.4 g product of formula II, wherein X is 2-methoxy-benzyl.

Rf = 0.60

$\lambda_{max}$ 427 nm ($E_{1cm}^{1\%}$ = 147), 302 nm ($E_{1cm}^{1\%}$ = 286)

I.R. 3350(b), 3200, 1738(Sh), 1722, 1650(Sh), 1620, 1570, 1520, 1500, 1320(b), 1250, 1165, 1125, 1066, 1030, 975, 950, 915, 886 and 810 cm$^{-1}$.

EXAMPLE 30

5 g 3-bromo-rifamycin S dissolved in 30 ml methanol were added to a solution of 3 g N-(1-hydroxymethyl-1-methyl-ethyl)-thiourea in 30 ml methanol at 10° C for 2 hours. A raw product was isolated that upon chromatography yielded 0.41 g product of formula II, wherein X is 1-hydroxymethyl-1-methyl-ethyl.

Rf = 0.53

$\lambda_{max}$ 425 nm ($E_{1cm}^{1\%}$ = 125), 307 nm ($E_{1cm}^{1\%}$ = 339)

I.R. 3400, 3100(b), 1720, 1650, 1595(Sh), 1565, 1525, 1315, 1265, 1240, 1225, 1160, 1100, 1060, 1020, 975, 955, 945, 915, 885 and 805 cm$^{-1}$.

EXAMPLE 31

4 g 3-bromo-rifamycin S in 50 ml methanol were reacted with 1.5 g N-(2-thienyl-methyl)-thiourea at 14° C for 2 hours. A raw product was isolated that, after chromatography on silica gel, yielded 0.86 g product of formula II, wherein X is 2-thienyl-methyl.

Rf = 0.60

$\lambda_{max}$ 431 nm ($E_{1cm}^{1\%}$ = 138), 307 nm ($E_{1cm}^{1\%}$ = 278)

I.R. 3350(b), 3200(b), 1740, 1725, 1655(Sh), 1620, 1574, 1525, 1315(b), 1260(Sh), 1240, 1160, 1064, 1020, 975, 950, 915, 883 and 805 cm$^{-1}$.

EXAMPLE 32

5 g 3-bromo-rifamycin S were dissolved in 50 ml methanol and added with 2 g N-(3-methoxy-propyl)-thiourea at 0° C for 2 hours. A raw product was isolated that was purified by chromatography on column, eluting with benzene and an acetone gradient from 85:15 to 70:30. 2 g products of formula II were obtained, wherein X is 3-methoxy-propyl.

Rf = 0.62

$\lambda_{max}$ 430 nm ($E_{1cm}^{1\%}$ = 159), 307 nm ($E_{1cm}^{1\%}$ = 321)

I.R. 3350(b), 3175(b), 1740(Sh), 1725, 1655(Sh), 1620, 1575, 1520, 1315(b), 1260(Sh), 1240, 1158, 1122, 1063, 1020, 975, 950, 915, 883 and 805 cm$^{-1}$.

What we claim is

1. A rifamycin compound having the formula:

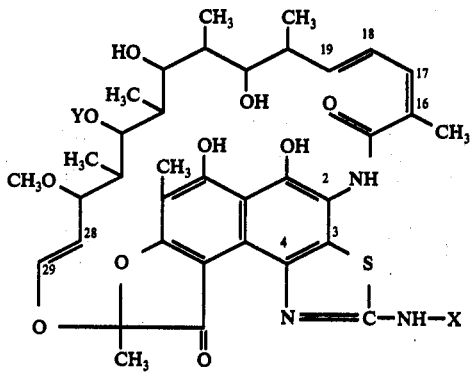

and its 16, 17, 18, 19 tetrahydroderivatives and 16, 17, 18, 19, 28, 29 hexahydroderivatives, wherein Y is —H or —COCH$_3$, and X is selected from the group consisting of hydrogen; C$_1$-C$_{12}$ alkyl; C$_3$-C$_4$ alkoxyalkyl; C$_2$-C$_4$ hydroxyalkyl; C$_4$-C$_6$ N,N-dialkylaminoalkyl; C$_7$-C$_8$ arylalkyl hydrocarbon; C$_3$-C$_7$ cycloalkyl; C$_3$-C$_6$ alkenyl; phenyl; C$_7$ arylalkyl hydrocarbon substituted in the aromatic ring with a radical selected from the group consisting of halogen, methyl, ethyl, propyl, butyl, methoxyl, N,N-dimethylamino; phenylmethylimino; furfuryl-2-methylimino; and a heterocyclic group selected from the group consisting of furfuryl, tetrahydrofurfuryl, 1,2,4-triazol-3-yl, thienylmethyl and 1,3-dimethyl-2,6-dioxo-1,2,3,6-tetrahydropyrimidine-4-yl.

2. A method for providing compounds of formula (II) according to claim 1, wherein a compound of formula:

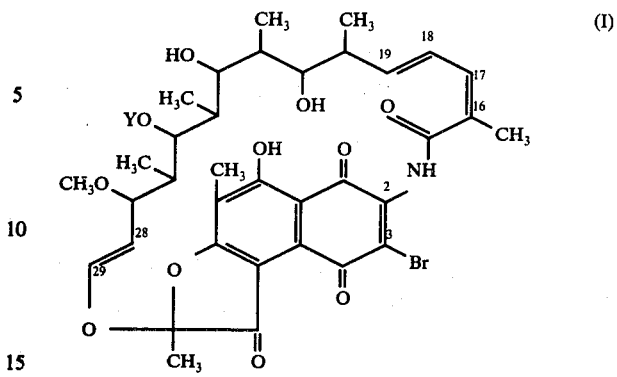
(I)

is dissolved in a solvent selected from the group comprising methanol, ethanol, tetrahydrofuran, and is then reacted with a compound of formula:

(III)

wherein X is as defined for the compound of formula (II), at a temperature in the range of −5° C and +40° C for a time of between 5 minutes and 25 hours.

* * * * *